(12) United States Patent
Di Fabio et al.

(10) Patent No.: US 7,462,622 B2
(45) Date of Patent: Dec. 9, 2008

(54) PYRROLO[2, 3-D] PYRIMIDINE DERIVATIVES AS CORTICOTROPIN RELEASING FACTOR ANTAGONISTS

(75) Inventors: Romano Di Fabio, Verona (IT); Chiara Marchionni, Verona (IT); Fabrizio Micheli, Verona (IT); Alessandra Pasquarello, Verona (IT); Bendetta Perini, Verona (IT); Yves St-Denis, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 444 days.

(21) Appl. No.: 10/480,958

(22) PCT Filed: Jun. 11, 2002

(86) PCT No.: PCT/GB02/02656

§ 371 (c)(1),
(2), (4) Date: Nov. 3, 2004

(87) PCT Pub. No.: WO02/100863

PCT Pub. Date: Dec. 19, 2002

(65) Prior Publication Data

US 2005/0054661 A1    Mar. 10, 2005

(30) Foreign Application Priority Data

Jun. 12, 2001 (GB) ................... 0114343.7
Jun. 12, 2001 (GB) ................... 0114349.4
Jul. 17, 2001 (GB) ................... 0177399.6

(51) Int. Cl.
  *A61K 31/519* (2006.01)
  *C07D 487/04* (2006.01)
  *A61P 25/24* (2006.01)
  *A61P 25/22* (2006.01)

(52) U.S. Cl. .................... 514/265.1; 544/280
(58) Field of Classification Search ............... 544/280; 514/265.1; 424/9.2
See application file for complete search history.

(56) References Cited

U.S. PATENT DOCUMENTS

2004/0171607 A1  9/2004  DiFabio et al. ......... 514/217.07
2004/0176400 A1  9/2004  Capelli et al. .......... 514/264.11

FOREIGN PATENT DOCUMENTS

EP      48/2804 A1    1/1997
WO      WO 95/33750   12/1995
WO      WO 99/11643 A1  3/1999

OTHER PUBLICATIONS

Ayala et al. (Exp. Opin. Ther. Patents, 2000, 10(1), 67-74).*
* cited by examiner

*Primary Examiner*—Brenda Coleman
*Assistant Examiner*—Susanna Moore
(74) *Attorney, Agent, or Firm*—Laura K. Madden; Loretta J. Sauermelch; Charles M. Kinzig

(57) ABSTRACT

The present invention provides compounds of formula (I) including stereoisomers, prodrugs and pharmaceutically acceptable salts or solvates thereof

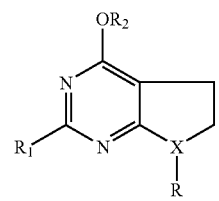

(I)

wherein
  R is aryl or heteroaryl and each of the above groups R may be substituted by 1 to 4 groups selected from:
    halogen, C1-C6 alkyl, C1-C6 alkoxy, halo C1-C6 alkyl, C2-C6 alkenyl, C2-C6 alkynyl, halo C1-C6 alkoxy, —COR$_4$, nitro, —NR$_3$R$_4$ cyano, or a group R$_5$;
  R$_1$ is hydrogen, C1-C6 alkyl, C2-C6 alkenyl, C2-C6 alkynyl, halo C1-C6 alkyl, halo C1-C6 alkoxy, halogen, NR$_3$R$_4$ or cyano;
  R$_2$ corresponds to a group CHR$_6$R$_7$;
  R$_3$ is hydrogen, C1-C6 alkyl;
  R$_4$ independently from R$_3$, has the same meanings;
  R$_5$ is C3-C7 cycloalkyl, which may contain one or more double bonds; aryl; or a 5-6 membered heterocycle; wherein each of the above groups R$_5$ may be substituted by one or more groups selected from: halogen, C1-C6 alkyl, C1-C6 alkoxy, halo C1-C6 alkyl, C2-C6 alkenyl, C2-C6 alkynyl, halo C1-C6 alkoxy, C1-C6 dialkylamino, nitro or cyano;
  R$_6$ is hydrogen, C2-C6 alkenyl or C1-C6 alkyl, wherein each of the above groups R$_6$ may be substituted by one or more groups selected from: C1-C6 alkoxy and hydroxy;
  R$_7$ independently from R$_6$, has the same meanings;
  X is carbon or nitrogen;
to processes for their preparation, to pharmaceutical compositions containing them and to their use in the treatment of conditions mediated by corticotropin-releasing factor (CRF).

9 Claims, No Drawings

PYRROLO[2, 3-D] PYRIMIDINE DERIVATIVES AS CORTICOTROPIN RELEASING FACTOR ANTAGONISTS

The present invention relates to bicyclic derivatives, to processes for their preparation, to pharmaceutical compositions containing them and to their use in therapy.

The first corticotropin-releasing factor (CRF) was isolated from ovine hypothalami and identified as a 41-amino acid peptide (Vale et al., Science 213: 1394-1397,1981).

CRF has been found to produce profound alterations in endocrine, nervous and immune system function. CRF is believed to be the major physiological regulator of the basal and stress-release of adrenocorticotropic hormone ("ACTH"), Bendorphin, and other pro-opiomelanocortin ("POMC")-derived peptides from the anterior pituitary (Vale et al., Science 213: 1394-1397,1981).

In addition to its role in stimulating the production of ACTH and POMC, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. Accordingly, clinical data suggests that CRF receptor antagonists may be useful in the treatment of the neuropsychiatric disorders manifesting hypersecretion of CRF, and, in particular, may represent novel antidepressant and/or anxiolytic drugs.

The first CRF receptor antagonists were peptides (see, e.g., Rivier et al., U.S. Pat. No. 4,605,642; Rivier et al., Science 224: 889, 1984). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported.

WO 95/10506 describes inter alia compounds of general formula A with general CRF antagonist activity

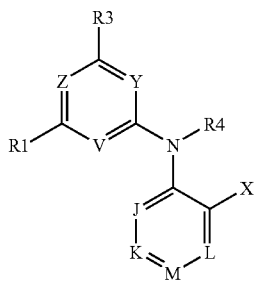

A wherein Y may be CR29; V and Z may be nitrogen and carbon, R3 may correspond to an ether derivative and R4 may be taken together with R29 to form a 5-membered ring and is —CH(R28) when R29 is —CH(R30).

There is no disclosure related to compounds corresponding to the above definition.

WO 95/33750 also describes compounds of general formula B having CRF antagonistic activity,

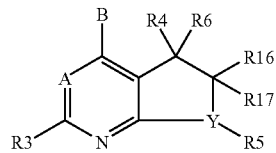

B in which A and Y may be nitrogen and carbon and B may correspond to an ether derivative. There is no disclosure related to compounds corresponding to the above definition.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

In particular the invention relates to novel compounds which are potent and specific antagonists of corticotropin-releasing factor (CRF) receptors.

The present invention provides compounds of formula (I) including stereoisomers, prodrugs and pharmaceutically acceptable salts or solvates thereof

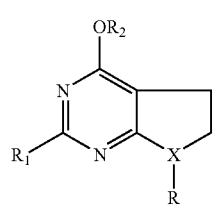

(I)

wherein
R is aryl or heteroaryl and each of the above groups R may be substituted by 1 to 4 groups selected from:
halogen, C1-C6 alkyl, C1-C6 alkoxy, halo C1-C6 alkyl, C2-C6 alkenyl, C2-C6 alkynyl, halo C1-C6 alkoxy, —COR$_4$, nitro, —NR$_3$R$_4$ cyano, or a group R$_5$;
R$_1$ is hydrogen, C1-C6 alkyl, C2-C6 alkenyl, C2-C6 alkynyl, halo C1-C6 alkyl, halo C1-C6 alkoxy, halogen, NR$_3$R$_4$ or cyano;
R$_2$ corresponds to a group CHR$_6$R$_7$;
R$_3$ is hydrogen, C1-C6 alkyl;
R$_4$ independently from R$_3$, has the same meanings;
R$_5$ is C3-C7 cycloalkyl, which may contain one or more double bonds; aryl;
or a 5-6 membered heterocycle;
wherein each of the above groups R$_5$ may be substituted by one or more groups selected from: halogen, C1-C6 alkyl, C1-C6 alkoxy, halo C1-C6 alkyl, C2-C6 alkenyl, C2-C6 alkynyl, halo C1-C6 alkoxy, C1-C6 dialkylamino, nitro or cyano;

$R_6$ is hydrogen, C6-C6 alkenyl or C1-C6 alkyl, wherein each of the above groups $R_6$ may be substituted by one or more groups selected from: C1-C6 alkoxy and hydroxy;

$R_7$ independently from $R_6$, has the same meanings;

X is carbon or nitrogen.

Acid addition salts of the free base amino compounds of the present invention may be prepared by methods well known in the art, and may be formed from organic and inorganic acids. Suitable organic acids include maleic, malic, fumaric, benzoic, ascorbic, succinic, methanesulfonic, p-toluensulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all acceptable salt forms.

The solvates may, for example, be hydrates.

References hereinafter to a compound according to the invention include both compounds of formula (I) and their pharmaceutically acceptable acid addition salts together with pharmaceutically acceptable solvates.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers.

All such isomeric forms are included within the present invention, including mixtures thereof. Furthermore, some of the crystalline forms of the compounds of structure (I) may exist as polymorphs, which are included in the present invention.

The term C1-C6 alkyl as used herein as a group or a part of the group refers to a linear or branched alkyl group containing from 1 to 6 carbon atoms; examples of such groups include methyl, ethyl, propyl, isopropyl, n-butyl, isobutyl, tert butyl, pentyl or hexyl.

The term C3-C7 cycloalkyl group means a non aromatic monocyclic hydrocarbon ring of 3 to 7 carbon atom such as, for example, cyclopropyl, cyclobutyl, cyclopentyl, cyclohexyl or cycloheptyl; while unsaturated cycloalkyls include cyclopentenyl and cyclohexenyl, and the like.

The term halogen refers to a fluorine, chlorine, bromine or iodine atom.

The term halo C1-C6 alkyl means an alkyl group having one or more carbon atoms and wherein at least one hydrogen atom is replaced with halogen such as for example a trifluoromethyl and the like.

The term C2-C6 alkenyl defines straight or branched chain hydrocarbon radicals containing one or more double bond and having from 2 to 6 carbon atoms such as, for example, ethenyl, 2-propenyl, 3-butenyl, 2-butenyl, 2-pentenyl, 3-pentenyl, 3-methyl-2-butenyl or 3-hexenyl and the like.

The term C1-C6 alkoxy group may be a linear or a branched chain alkoxy group, for example methoxy, ethoxy, propoxy, prop-2-oxy, butoxy, but-2-oxy or methylprop-2-oxy and the like.

The term halo C1-C6 alkoxy group may be a C1-C6 alkoxy group as defined before substituted with at least one halogen, preferably fluorine, such as difluoromethoxy, or trifluoromethoxy.

The term C2-C6 alkynyl defines straight or branched chain hydrocarbon radicals containing one or more triple bond and having from 2 to 6 carbon atoms including acetylenyl, propynyl, 1-butynyl, 1-pentynyl, 3-methyl-1-butynyl and the like.

The term aryl means an aromatic carbocyclic moiety such as phenyl, biphenyl or naphthyl.

The term heteroaryl means an aromatic heterocycle ring of 5- to 10 members and having at least one heteroatom selected from nitrogen, oxygen and sulfur, and containing at least 1 carbon atom, including both mono-and bicyclic ring systems.

Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, triazolyl, tetrazolyl, and quinazolinyl.

The term 5-6 membered heterocycle means, according to the above definition, a monocyclic heterocyclic ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized. The heterocycle may be attached via any heteroatom or carbon atom. Thus, the term include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

Thus, representative compounds of this invention include the following structure (Ia) and (Ib), depending upon the meaning of X according to the definition of compounds (I) given above, and in which R, $R_1$ and $R_2$ are defined as before:

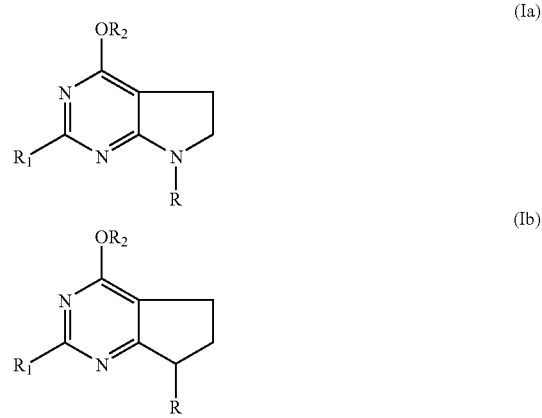

Compounds of formula (Ia) are particularly preferred.

Even more preferred embodiments of the invention include, but are not limited to, compounds of the formula (I), (Ia), and (Ib):

wherein:

R₁ is C1-3 alkyl or halo C1-C3 alkyl, preferably methyl or trifluoromethyl;

R is an aryl group selected from: 2,4-dichlorophenyl, 2-chloro-4-methylphenyl, 2-chloro-4-trifluoromethyl, 2-chloro-4-methoxyphenyl, 2,4-dimethylphenyl, 2-methyl-4-methoxyphenyl, 2-methyl-4-chlorophenyl, 2-methyl-4-trifluoromethyl, 2,4-dimethoxyphenyl, 2-methoxy-4-trifluoromethylphenyl, 2-methoxy-4-chlorophenyl, 3-methoxy-4-chlorophenyl, 2,5-dimethoxy-4-chlorophenyl, 2-methoxy-4-isopropylphenyl, 2-methoxy-4-trifluoromethylphenyl, 2-methoxy-4-isopropylphenyl, 2-methoxy-4-methylphenyl, 2-trifluoromethyl-4-chlorophenyl, 2,4-trifluoromethylphenyl, 2-trifluoromethyl-4-methylphenyl, 2-trifluoromethyl-4-methoxyphenyl, 2-bromo-4-isopropylphenyl, 4-methyl-6-dimethylaminopyridin-3-yl, 4-dimethylamino-6-methylpyridin-3-yl, 6-dimethylamino-pyridin-3-yl and 4-dimethylaminopyridin-3-yl.

Preferred compounds according to the invention are:

7-(2,4 chlorophenyl)-4-(1-ethyl-propoxy)-2-methyl-6,7-dihydro-5H-pyrrolo[2,3-d]-pyrimidine (1-1);

7-(2,4-dichlorophenyl)-4-(1-isopropyl-2-methyl-propoxy)-2-methyl-6,7-dihydro-5H-pyrrolo-[2,3-d]pyrimidine (1-2);

7-(2,4-dichlorophenyl)-4-(1-isopropyl-3-methyl-butoxy)-2-methyl-6,7-dihydro-5H-pyrrolo-[2,3-d]pyrimidine (1-3);

7-(2,4-dichlorophenyl)-4-(2-methoxy-1-methoxymethyl-ethoxy)-2-methyl-6,7-dihydro-5H-pyrrolo[2,3-d]pyrimidine (1-1-4);

7-(2,4-dichlorophenyl)-4-(2-ethyl-butoxy)-2-methyl-6,7-dihydro-5H-pyrrolo[2,3-d]-pyrimidine (1-5);

7-(2,4-dichlorophenyl)-4-(2-ethoxy-1-ethoxymethyl-ethoxy)-2-methyl-6,7-dihydro-5H-pyrrolo[2,3-d]pyrimidine (1-6);

7-(2,4-bis-trifluoromethyl-phenyl)-4-(1-ethyl-propoxy)-2-methyl-6,7-dihydro-5H-pyrrolo[2,3-d]pyrimidine (1-7);

7-(2,4-dichlorophenyl)4-(1-ethyl-2-methyl-allyloxy)-2-methyl-6,7-dihydro-5H-pyrrolo[2,3-d]pyrimidine (1-8);

7-(2,4-dichlorophenyl)4-(1-methoxymethyl-propoxy)-2-methyl-6,7-dihydro-5H-pyrrolo[2,3-d]pyrimidine (1-9);

2-[7-(2,4-dichlorophenyl)-2-methyl-6,7-dihydro-5H-pyrrolo[2,3-d]pyrimidin-4-yloxy]butan-1-ol (1-10);

7-(2,4-bis-trifluoromethyl-phenyl)-4-(1-methoxymethyl-propoxy)-2-methyl-6,7-dihydro-5H-pyrrolo[2,3-d]pyrimidine (1-12);

4-[4-(1-ethyl-propoxy)-2-methyl-5,6-dihydro-pyrrolo[2,3-d]pyrimidin-7-yl]-3-trifluoromethyl-benzamide (1-13);

4-(1-ethyl-propoxy)-7-[2-(1-ethyl-propoxy)-6-trifluoromethyl-pyridin-3-yl]-2-methyl-6,7-dihydro-5H-pyrrolo[2,3-d]pyrimidine (1-14);

2-[4-(1-ethyl-propoxy)-2-methyl-5,6-dihydro-pyrrolo[2,3-d]pyrimidin-7-yl]-5-trifluoromethyl-benzonitrile (1-15).

In general, the compounds of structure (I) may be made according to the organic synthesis techniques known to those skilled in this field, as well as by the representative methods set forth in the Examples.

Compounds of formula (I), and salts and solvates thereof, may be prepared by the general methods outlined hereinafter. In the following description, the groups R, R₁, R₂, R₃, R₄, R₅, R₆, R₇ X and n have the meaning as previously defined for compounds of formula (I) unless otherwise stated.

Compounds of formula (I), may be prepared by reaction of a compound of formula (II)

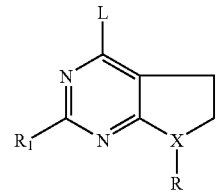

(II)

wherein L is a leaving group, preferably an halogen group (e.g. chlorine) with the alcohol compound (III)

HOCHR₂ₐR₃ₐ  (III)

wherein R₂ₐ and R₃ₐ have the meanings defined above for R₂ and R₃ or are a group convertible thereto.

The reaction can be optionally carried out in an aprotic solvent such as N,N-dimethylformamide in the presence of a strong base such as sodium hydride and with heating. For the preparation of the compounds of formula (I), wherein R₃ and/or R₂ are/is hydroxy, the reaction is conveniently carried out using an intermediate of formula (II) in which R₃ₐ and/or R₂ₐ are/is a protected hydroxyl group.

When the group R₃ₐ and/or R₂ₐ are/is a protected hydroxyl group this is conveniently an ether or an acyloxy group. Examples of suitable ethers include trityl ether, hydrocarbylsilyl group such as trialkylsilyl e.g. trimethylsilyl or t-butyldimethylsilyl. When the protected hydroxyl group represents an acyloxy group, examples of suitable groups include alkanoyl e.g. acetyl, pivaloyl; alkenoyl e.g. allylcarbonyl; aroyl e.g. pnitrobenzoyl; alkoxycarbonyl e.g. t-butoxycarbonyl.

Compounds of formula (IIa), equivalent to compounds of formula (II) in which X is nitrogen, may be prepared by cyclisation of a compound of formula (IV).

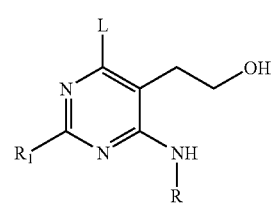

(IV)

The cyclisation takes place in an aprotic solvent such as tetrahydrofuran and in the presence of a tertiary amine such as triethyl amine and mesyl chloride.

Compounds of formula (IV) may be prepared by oxidation of a compound of formula (V)

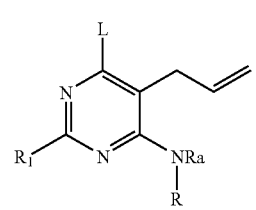

(V)

wherein $R_a$ is a suitable nitrogen protecting group, to the corresponding aldehyde followed by reduction to alcohol and removal of the nitrogen protecting group.

The oxidation is carried out with ozone at low temperature, e.g. −78° C., in a solvent such as dichloromethane.

The reduction takes places using for example sodium borohydride in a solvent such as alcohol.

Examples of suitable nitrogen protecting group include alkoxycarbonyl, e.g. t-butoxycarbonyl and arylsulphonyl, e.g phenylsulphonyl.

Compounds of formula (V) may be prepared by reaction of a compound of formula (VI), wherein L is defined as above, with amine (VII).

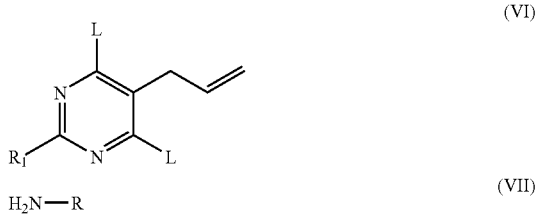

The reaction preferably takes place in an aprotic solvent such as tetrahydrofuran, dichlorometane or N,N-dimethyl formamide in the presence of a strong base such sodium hydride and with heating.

Compounds of formula (VI) and (VII) are either known compounds or may be prepared by analogous method to those described for known compounds.

Compounds of formula (IIb), equivalent to compounds of formula (II) in which X is a carbon atom, may be prepared by conversion of the hydroxy group of compounds of formula (VIII) into a leaving group.

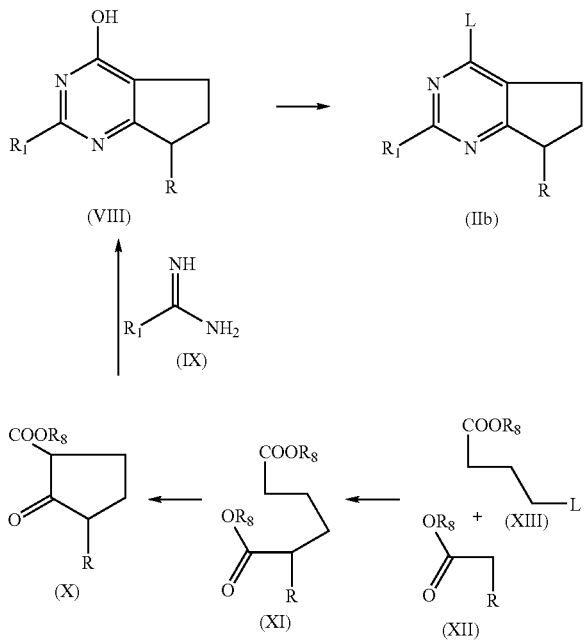

For example, the halogenation reaction may be carried out using conventional methods known in the art Thus, e.g. the reaction may be carried out by treatment with $PO(Hal)_3$, wherein Hal is preferably chlorine.

Compounds of formula (VIII) may be prepared by cyclisation of a compound of formula (X) with a salt (e.g. hydrochloride) of acetamidine (IX).

The reaction is carried out in the presence of an alkaline organic base C1-C4 (e.g. sodium methoxide) in a solvent such as methyl alcohol.

Compounds of formula (X) may be prepared by cyclisation of a compound of formula (XI), in which $R_8$ is a linear or branched C1-C4 alkyl and p is defined as above.

The cyclisation may be carried out in the presence of an organic alkaline C1-C4 alkoxyde (e.g sodium methoxide) in an aprotic solvent such as N,N-dimethylformamide or toluene and at temperature ranging from 20° to 100° C.

Compounds of formula (XI) can be prepared by reaction of a compound of formula (XII) with a compound of formula (XIII), wherein L is preferably a bromine or iodine atom.

The reaction is carried out in aprotic solvent such as an ether e.g. tetrahydrofuran at low temperature, e.g. −78° C., and in the presence of a strong base such as Lithium diisopropylamide.

Alternatively, compounds of formula (X) may be prepared according to the following scheme from 2-chloro-cyclopentanone, by reaction with a suitable Grignard derivative of the group R and then carboxymethylated as described above.

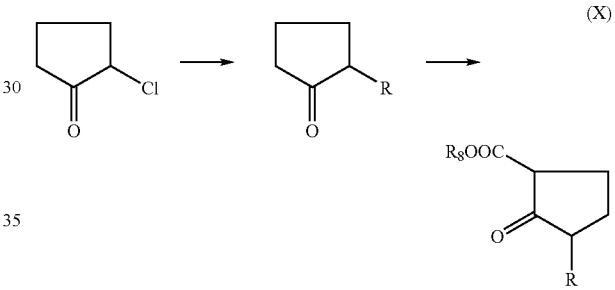

In any of the above reaction the nitrogen protecting group and hydroxyl protecting group may be removed by conventional procedures known for removing such groups (such as those described in Protective Groups in Organic Chemistry, pages 46-119, Edited by J F W McOmie (Plenum Press, 1973)).

Thus, when $R_a$ is alkoxycarbonyl, the group may be removed by acid hydrolisis using for example trifluoro acetic acid.

When, for example, the hydoxyl protecting group is a trityl ether, the group may be removed by acid hydrolisis using for example trifluoro acetic acid.

Pharmaceutical acceptable salts may also be prepared from other salts, including other pharmaceutically acceptable salts, of the compound of formula (I) using conventional methods.

The compounds of formula (I) may readily be isolated in association with solvent molecules by crystallisation or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The invention as herein described also includes isotopically-labeled compounds, which are identical to those falling within the scope of formulas I, Ia and Ib, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{18}$F, $^{123}$I and $^{125}$I.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^8$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of this invention can generally be prepared by carrying out the procedures disclosed in the Schemes and/or in the Examples below, by substituting a readily available isotopically labeled reagent for a non-isotopically labeled reagent.

In another aspect of the present invention, the compounds of formula (I) in which $R_2$ represents —$CHR_6R_7$, wherein $R_6$ or $R_7$ are defined as before and are substitueted by an isotopically labeled C1-6 alkoxy group, preferably an isotopically labeled methoxy group, may be very useful for the scope outlined before.

In particular, the compounds (1-9) and (1-12), whose preparation is reported in Example 1, show a good activity and may be easily prepared in a radiolabeled form as described above. These radiolabeled compounds may be easily prepared according to the following process, starting from the hydroxy precursors.

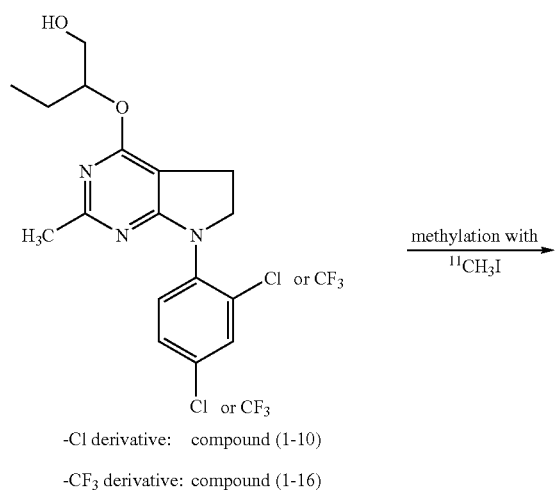

-Cl derivative: compound (1-10)

-CF$_3$ derivative: compound (1-16)

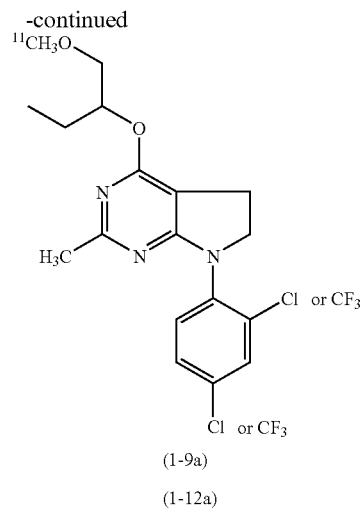

(1-9a)

(1-12a)

According to this process, the hydroxy precursors of radiolabeled compounds (1-9a) and (1-12a), compounds (1-10) and (1-16) described in Example 1 are methylated with $^{11}$CH$_3$I, following the procedure described in Examples 4 and 5.

The CRF receptor antagonists of the present invention demonstrate activity at the CRF receptor site including CRF 1 and CRF 2 receptors and may be used in the treatment of conditions mediated by CRF or CRF receptors.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (J. Neuroscience 7: 88,1987) and Battaglia et al. (Synapse 1: 572,1987).

The CRF receptors-binding assay was performed by using the homogeneous technique of scintillation proximity (SPA). The ligand binds to recombinant membrane preparation expressing the CRF receptors which in turn bind to wheat germ agglutinin coated SPA beads. In the Experimental Part will be disclosed the details of the experiments.

With reference to CRF receptor binding affinities, CRF receptor antagonists of this invention have a Ki less than 10 μm.

In a preferred embodiment of this invention, a CRF receptor antagonist has a Ki less than 1 μm.

In a more preferred embodiment the value of Ki is less than 0.1 μM and more preferably less than 0.01 μm. As set forth in greater detail below, the Ki values of representative compounds of this invention were assayed by the methods set forth in Example 2.

Preferred compounds having a Ki of less than 1 μm are compound numbers 1-5, 1-6, and 1-14.

More preferred compounds having a Ki less than 0.1 μm are compound numbers 1-2, 1-4, 1-8, 1-10, 1-13 and 1-15.

Even more preferred compounds having a Ki less than 0.1 μm are compound numbers 1-1, 1-3, 1-7, 1-9 and 1-12.

Compounds of the invention are useful in the treatment of central nervous system disorders where CRF receptors are involved. In particular in the treatment or prevention of major depressive disorders including bipolar depression, unipolar depression, single or recurrent major depressive episodes with or without psychotic features, catatonic features, melancholic features, atypical features or postpartum onset, the treatment of anxiety and the treatment of panic disorders. Other mood disorders encompassed within the term major depressive disorders include dysthymic disorder with early or late onset and with or without atypical features, neurotic depression, post traumatic stress disorders and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

Compounds of the invention are useful as analgesics. In particular they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch; and thalamic pain such as post stroke thalamic pain.

Compounds of the invention are also useful for the treatment of dysfunction of appetite and food intake and in circumstances such as anorexia, anorexia nervosa and bulimia.

Compounds of the invention are also useful in the treatment of sleep disorders including dysomnia, insomnia, sleep apnea, narcolepsy, and circadian ritmic disorders.

Compounds of the invention are also useful in the treatment or prevention of cognitive disorders. Cognitive disorders include dementia, amnestic disorders and cognitive disorders not otherwise specified.

Furthermore compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds), or in the treatment of tolerance to and dependence on opiates (e.g. cannabis, heroin, morphine) or benzodiazepines; in the treatment of cocaine, sedative ipnotic, amphetamine or amphetamine-related drugs (e.g. dextroamphetamine, methylamphetamine) addiction or a combination thereof.

Compounds of the invention are also useful as anti-inflammatory agents. In particular they are useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease (IBD) and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of allergic disorders, in particular allergic disorders of the skin such as urticaria, and allergic disorders of the airways such as rhinitis.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, waterbrash/regurgitation, heartburn, such as episodic heartburn, nocturnal heartburn, and meal-induced heartburn and dyspepsia.

Compounds of the invention are of particular use in the treatment of gastrointestinal disorders such as irritable bowel syndrome (IBS); skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Compounds of the invention are useful for the treatment of neurotoxic injury which follows cerebral stroke, thromboembolic stroke, hemorrhagic stroke, cerebral ischemia, cerebral vasospam, hypoglycemia, hypoxia, anoxia, perinatal asphyxia cardiac arrest.

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by CRF.

In an alternative or further aspect there is provided a method for the treatment of a mammal, including man, in particular in the treatment of condition mediated by CRF, comprising administration of an effective amount of a compound of formula (I) or a pharmaceutically acceptable salt or a solvate thereof.

It will be appreciated that reference to treatment is intended to include prophylaxis as well as the alleviation of established symptoms.

Compounds of formula (I) may be administered as the raw chemical but the active ingredient is preferably presented as a pharmaceutical formulation.

Accordingly, the invention also provides a pharmaceutical composition which comprises at least one compound of formula (I) or a pharmaceutically acceptable salt thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus compounds of formula (I) may be formulated for oral, buccal, parenteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device.

A proposed dose of the compounds of the invention is 1 to about 1000 mg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

Thus for parenteral administration a daily dose will typically be in the range of 1 to about 100 mg, preferably 1 to 80 mg per day. For oral administration a daily dose will typically be within the range 1 to 300 mg e.g. 1 to 100 mg.

EXAMPLES

In the Intermediates and Examples unless otherwise stated:

Melting points (m.p.) were determined on a Gallenkamp m.p. apparatus and are uncorrected. All temperatures refers to ° C. Infrared spectra were measured on a FT-IR instrument. Proton Magnetic Resonance ($^1$H-NMR) spectra were recorded at 400 MHz, chemical shifts are reported in ppm downfield (d) from $Me_4Si$, used as internal standard, and are assigned as singlets (s), doublets (d), doublets of doublets (dd), triplets (t), quartets (q) or multiplets (m). Column chromathography was carried out over silica gel (Merck AG Darmstaadt, Germany). The following abbreviations are used in text: EtOAc=ethyl acetate, cHex=cyclohexane, $CH_2Cl_2$=dichloromethane, $Et_2O$=dietyl ether, DMF=N,N'-dimethylformamide, DIPEA=N,N-diisopropylethylamine MeOH=methanol, $Et_3N$=triethylamine, TFA=trifluoroacetic acid, THF=tetrahydrofuran, DIBAL-H=diisobutylaluminium hydride, DMAP=dimethylaminopyridine, LHMDS=lithiumhexamethyldisilazane; Tlc refers to thin layer chromatography on silica plates, and dried refers to a solution dried over anhydrous sodium sulphate; r.t. (RT) refers to room temperature.

Intermediate 1

5-Allyl-4,6-dihydroxy-2-methyl-pyrimidine

Sodium (2 g) was added portionwise to anh. MeOH (100 ml), at 0° C., under $N_2$. After consumption of metallic sodium, acetamidine hydrochloride (8.4 g) was added. After 10 min. of stirring the precipitated NaCl was filtered off. Diethyl-allyl-malonate (6 ml) was added to the solution of free acetamidine and the mixture was stirred at r.t. for 2 days. The reaction mixture was concentrated and then neutralized with concentrated hydrochloric acid, filtered to obtain the title compound as a white solid (4.25 g).

NMR ($^1$H, DMSO-d$_6$): δ 11.61 (bs, 2H), 5.75 (m, 1H), 4.92 (m, 1H), 4.84 (m, 1H), 2.94 (d, 2H), 2.19 (s, 3H).

MS (m/z): 166 [M]$^+$.

Intermediate 2

5-Allyl-4,6-dichloro-2-methyl-pyrimidine

Intermediate 1 (6.0 g) was mixed with POCl$_3$ (70 ml) and heated at reflux for 3 hr. The resulting solution was cooled to r.t. and poured slowly into ice/water (600 ml) with vigorous stirring. The product was extracted with EtOAc (3×50 ml). The combined organic extracts were washed with saturated NaHCO$_3$ (60 ml) and brine (40 ml), dried over Na$_2$SO$_4$, filtered and concentrated in vacuo. The crude oil was purified by flash chromatography (silica gel, cHex 100%). The title compound was obtained as a light yellow oil (4.78 g).

NMR ($^1$H, CDCl$_3$): δ 5.85 (m, 1H), 5.15 (dq, 1H), 5.11 (dq, 1H), 3.61 (dt, 2H), 2.67 (s, 3H).

MS (m/z): 202 [M]$^+$ 0.2Cl; 167 [MH—Cl]$^+$, 1 Cl.

Intermediate 3

(5-Allyl-6-chloro-2-methyl-pyrimidin-4-yl)-(2,4-dichloro-phenyl)-amine

A solution of 2,4-dichloroaniline (798 mg) in anh. THF (22 ml), under N$_2$, was treated with sodium hydride (95% in mineral oil, 393 mg) at 0° C. for 15 min before intermediate 2 (1 g) was added. The mixture was heated at reflux for 3 hr and quenched with water (20 ml). The product was extracted with ethyl acetate (2×20 ml), dried over Na$_2$SO$_4$ and concentrated in vacuo. The crude product was purified by flash chromatography (silica gel, EtOAc/cHex 4/96) to give the title compound as a white solid (725 mg).

NMR ($^1$H, CDCl$_3$): δ 8.52 (d, 1H), 7.40 (d, 1H), 7.27 (dd, 1H), 7.21 (bs, 1H), 5.90 (m, 1H), 5.26 (m, 2H), 3.58 (m, 2H), 2.57 (s, 3H).

MS (m/z): 327 [M]$^+$, 3Cl.

Intermediate 4

(5-Allyl-6-chloro-2-methyl-pyrimidin-4yl)-2,4dichloro-phenyl) carbamic acid tert-butyl ester To a solution of intermediate 3 (146 mg) in anh. CH$_2$Cl$_2$ (11 ml), under N$_2$, was added (Boc)$_2$O (194 mg) and DMAP (cat). The reaction mixture was stirred at r.t. for 18 hr. The solution was diluted with water (10 ml) and extracted with EtOAc (3×15 ml). The combined organic extracts were dried over anh. Na$_2$SO$_4$, filtered and concentrated to dryness in vacuo. Flash chromatography of the crude product (silica gel, cHex/EtOAc 95:5) gave the title compound as colourless oil (164 mg)

NMR ($^1$H, CDCl$_3$): δ 7.47 (d, 1H), 7.20 (dd, 1H), 7.17 (d, 1H), 5.75 (tq, 1H), 5.05 (dd, 1H), 4.97 (dd, 1H), 3.52 (d, 2H), 2.58 (s, 3H), 1.44 (s, 9H).

IR (nujol, cm$^{-1}$): 1729.

MS (m/z): 428 [MH]$^+$, 3Cl; 372 [MH-tBu+H]$^+$, 328 [MH-Boc+H]$^+$

Intermediate 5

[6-Chloro-5-(2-hydroxy-ethyl)-2-methyl-pyrimidinyl-4-yl]-(2,4dichloro-phenyl)carbamic acid tert-butyl ester A solution of intermediate 4 (160 mg) in CH$_2$Cl$_2$ (9 ml) and CH$_3$OH (1 ml) was ozonized (5 g.h$^{-1}$) at −78° C. for 10 min. When all the allyl pyrimidine had disappeared (according to tlc), the reaction mixture was first flushed with oxygen and then with nitrogen for 20 min. To the cooled reaction mixture was added NaBH$_4$ (56 mg) and the temperature was allowed to warm up to r.t. The solution was stirred for 3 hr at r.t. It was then diluted with water (10 ml) and extracted with CH$_2$Cl$_2$ (3×10 ml). The combined organic extracts were dried over anh. Na$_2$SO$_4$, filtered and concentrated to dryness in vacuo. The crude product was purified by flash chromatography (silica gel, cHex/EtOAc 85:15) to give the title compound as white solid (120 mg).

NMR ($^1$H, CDCl$_3$): δ 7.49 (d, 1H), 7.37 (d, 1H), 7.23 (dd, 1H), 3.93 (q, 2H), 3.05 (t, 2H), 2.59 (s, 3H), 1.89 (bs, 1H), 1.45 (s, 9H).

IR (nujol, cm$^{-1}$): 3430, 1717.

MS (m/z): 432 [MH]$^+$, 3Cl; 454 [MH+Na]$^+$, 332 [MH-Boc+H]$^+$

Intermediate 6

Methanesulfonic acid 2-{4-tert-butoxcarbonyl(2.4-dichloro-phenyl)amino]-6-chloro-2-methyl-pyrimidin-5-yl}ethyl ester To a solution of intermediate 5 (337 mg) in anh. CH$_2$Cl$_2$ (15 ml), at r.t, under N$_2$, was added Et$_3$N (545µl) and CH$_3$SO$_2$Cl (120 µl). The reaction was stirred at r.t. for 18 hr. Water (15 ml) and EtOAc (15 ml) were added, the phases were separated and the aqueous layer was extracted with additional EtOAc (2×15 ml). The combined organic extracts were washed with H$_2$O (20 ml), dried over Na$_2$SO$_4$, filtered and concentrated in vacuo. The crude product was purified by flash chromatography (silica gel, cHex/EtOAc 75:25) to give the title compound as a white foam (327 mg).

NMR ($^1$H, CDCl$_3$): δ 7.49 (d, 1H), 7.34 (d, 1H), 7.26 (m, 1H), 4.52 (t, 2H), 3.24 (t, 2H), 2.98 (s, 3H), 2.58 (s, 3H), 1.45 (s, 9H).

MS (m/z): 510 [MH]$^+$, 3Cl; 532 [MH+Na]$^+$, 454 [MH-tBu+H]$^+$, 410 [MH-Boc+H]$^+$

Intermediate 7

Methanesulfonic acid 2-[4-chloro-6-(2,4-dichloro-phenylamino)-2-methyl-pyrimidin-5-yl]-ethyl ester A solution of intermediate 6 (327 mg) in 20% TFA in CH$_2$Cl$_2$ (10 ml) was stirred at r.t. for 2 hr. The solvent was removed in vacuo and the residue was partitioned between EtOAc (10 ml) and sat. aq. NaHCO$_3$ (10 ml), and the layers were separated. The aqueous layer was extracted with EtOAc (3×10 ml), and the combined organic extracts were dried over Na$_2$SO$_4$, filtered and concentrated to dryness in vacuo to obtain the title compound as white solid (224 mg).

NMR ($^1$H, CDCl$_3$): δ 8.39 (d, 1H), 7.49 (d, 1H), 7.44 (bs, 1H), 7.34 (dd, 1H), 4.56 (t, 2H), 3.28 (t, 2H), 3.03 (s, 3H), 2.61 (s, 3H).

MS (m/z): 410 [MH]$^+$, 3Cl.

Intermediate 8

4-Chloro-7-(2,4-dichloro-phenyl)-2-methyl-6,7-dihydro-5H-pyrrolo[2,3-d]pyrimidine To a solution of intermediate 7 (224 m) in anh. THF (10 ml) was added, at r.t., under $N_2$, NaH (95% mineral oil, 20 mg). The reaction was stirred for 2 hr at r.t. The solution was diluted with water (10 ml) and extracted with EtOAc (2×15 ml). The combined organic extracts were dried over anh. $Na_2SO_4$, filtered and concentrated to dryness in vacuo. The crude product was purified by flash chromatography (silica gel, cHex/EtOAc 75:25) to give the title compound as a white solid (158 mg).

NMR ($^1$H, $CDCl_3$): δ 7.51 (s, 1H), 7.33 (m, 2H), 4.04 (t, 2H), 3.21 (t, 2H), 2.44 (s, 3M).

MS (m/z): 313[MH]$^+$, 3Cl

Intermediate 9

(5-Allyl-6-chloro-2-methyl-pyrimidin-4-yl)-(2,4-bis-trifluoromethyl-phenyl)-amine A solution of 2,4-bis-trifluoromethyl-aniline (563 mg) in anh. THF (4 ml), at r.t., under $N_2$, was treated with sodium hydride (80% in mineral oil, 111 mg) at 0° C. for 15 min. Intermediate 2 (500 mg) was then added. The mixture was heated to reflux for 3 hr and quenched with water (10 ml). The aqueous layer was extracted with EtOAc (3×15 ml). The combined organic extracts were dried over $Na_2SO_4$, the solids were filtered and the solvent evaporated in vacuo. The crude product was purified by flash chromatography (silica gel, EtOAc/cHex 4:96) to give the title compound as a brown oil (260 mg).

NMR ($^1$H, $CDCl_3$): δ 8.55 (d, 1H), 7.88 (bs, 1H), 7.83 (bd, 1H), 7.19 (bs, 1H), 5.92 (m, 1H), 5.27 (m, 1H), 5.17 (m, 1H), 3.56 (m, 2H), 2.58 (s, 3H).

MS (m/z): 396 [MH]$^+$.

Intermediate 10

(5-Allyl-6-chloro-2-methyl-pyrimidin-4-yl)-(2,4-bis-trifluoromethyl-phenyl) carbamic acid tert-butyl ester To a solution of intermediate 9 (435 mg) in anh. $CH_2Cl_2$ (3 ml), under $N_2$, at r.t., was added $(Boc)_2O$ (336 mg) and DMAP (cat). The reaction was stirred at r.t. for 40 hr. The solution was diluted with water (10 ml) and extracted with EtOAc acetate (3×15 ml). The combined organic extracts were dried over anh. $Na_2SO_4$, the solids were filtered and the solvent was evaporated to dryness in vacuo. Flash chromatography of the crude product (silica gel, cHex/EtOAc 96:4) gave the title compound as a yellow oil (460 mg)

NMR ($^1$H, $CDCl_3$): δ 7.96 (s, 1H), 7.83 (d, 1H), 7.55 (d, 1H), 5.90 (m, 1H), 5.18 (dd, 1H), 5.13 (d, 1H), 3.56 (m, 2H), 2.50 (s, 3H), 1.41 (s, 9H).

IR (nujol, $cm^{-1}$): 1726.

MS (m/z): 496 [MH]$^+$; 440 [MH-tBu+H]$^+$; 396 [MH-BOC+H]$^+$.

Intermediate 11

(2,4-Bis-trifluoromethyl-phenyl)-[6-chloro-5-(2-hydroxy-ethyl)-2-methyl-pyrimidin-4-yl]-carbamic acid tert-butyl ester A solution of intermediate 10 (460 mg) in anh. $CH_2Cl_2$ (9 ml) and $CH_3OH$ (1 ml) was ozonized (5 g.h$^{-1}$) at −78° C. for 20 min. When all the starting material had disappeared (according to tlc in cHex/EtOAc 7:3), the reaction mixture was first flushed with oxygen and then with nitrogen for 5 min. To the cooled reaction mixture was added $NaBH_4$ (137 mg) and the temperature was allowed to warm up to r.t. The solution was stirred for 1.5 hr at r.t. It was then diluted with water (10 ml) and extracted with $CH_2Cl_2$ (3×10 ml). The combined organic extracts were dried over anh. $Na_2SO_4$, the solids were filtered and the solvent evaporated to dryness in vacuo. The crude product was purified by flash chromatography (silica gel, cHex/EtOAc 9:1) to give the title compound as white solid (385 mg).

NMR ($^1$H, $CDCl_3$): δ 7.96 (bs, 1H), 7.86 (bd, 1H), 7.74 (d, 1H), 4.13-4.05 (m, 2H), 3.07 (td, 2H), 2.49 (s, 3H), 2.21 (bs, 1H), 1.41 (s, 9H).

IR (nujol, $cm^{-1}$): 1724, 1602.

MS (m/z): 500 [MH]$^+$; 444 [MH-tBu+H]$^+$; 400 [MH-Boc+H]$^+$.

Intermediate 12

Methanesulfonic acid 2-[4-(2,4-bis-trifluoromethyl-phenylamino)-6-chloro-2-methyl-pyrimidin-5-yl]-ethyl ester To a solution of intermediate 11 (385 mg) in anh. $CH_2Cl_2$ (5 ml), at r.t, under $N_2$, were added $Et_3N$ (540 μl) and $CH_3SO_2Cl$ (120 μl). The reaction mixture was stirred at r.t. for 18 hr. Water (15 ml) and $CH_2Cl_2$ (15 ml) were added and the phases were separated. The aqueous layer was extracted with $CH_2Cl_2$ (2×15 ml). The combined organic extracts were dried over $Na_2SO_4$, the solids filtered and the solvent evaporated in vacuo.

A solution of the crude product in 20% TFA/$CH_2Cl_2$ (4 ml) was stirred at r.t. for 2 hr. The solvent was removed in vacuo and the residue was redissolved in EtOAc (10 ml) and sat. aq. $NaHCO_3$ (10 ml). The phases were separated and the aqueous layer was extracted EtOAc (3×10 ml). The combined organic extracts were dried over $Na_2SO_4$, the solids were filtered and the solvent evaporated to dryness in vacuo to deliver the title compound as a yellow solid (322 mg).

NMR ($^1$H, $CDCl_3$): δ 9.09 (bs, 1H), 8.12 (d, 1H), 8.09 (s, 1H), 7.74 (d, 1H), 4.36 (t, 2H), 3.23 (t, 2H), 3.15 (s, 3H), 2.19 (s, 3H).

IR ($CDCl_3$, $cm^{-1}$): 1346, 1177

MS (m/z): 478[MH]$^+$.

Intermediate 13

7-(2,4-Bis-trifluoromethyl-phenyl)-4chloro-2-methyl-6,7-dihydro-5H-pyrrolo[2,3-d]pyrimidine To a solution of intermediate 12 (320 mg) in anh. THF (8 ml) was added, at r.t., under $N_2$, NaH (80% mineral oil, 30 mg). The reaction mixture was stirred for 2 hr at 60° C. It was then diluted with water (10 ml) and extracted with EtOAc (2×15 ml). The combined organic extracts were dried over anh. $Na_2SO_4$, the solids were filtered and the solvent evaporated to dryness in vacuo. The crude product was purified by flash chromatography (silica gel, cHex/EtOAc 90:10) to give the title compound as a white solid (154 mg).

Alternatively, intermediate 13 can be prepared from intermediate 24 as follows:

To a solution of intermediate 24 (514 mg, 1.29 mmol) in anh. $CH_2Cl_2$ (20 mL), at 0° C., under $N_2$, were added $Et_3N$ (712 μL, 4 eq)) and mesyl chloride (197 μL, 2 eq) and the reaction mixture was stirred at r.t. for 18 hr. Water (20 mL) was then added and the phases were separated. The aqueous layer was extracted with $CH_2Cl_2$ (2×20 mL) and the combined organic extracts were dried over anh. $Na_2SO_4$. The solids were filtered and the solvent was evaporated. The crude product was purified by flash chromatography (silica gel, 8:2 cHex/EtOAc) to give the title compound as a white solid (430 mg, 87%).

NMR ($^1$H, $CDCl_3$): δ 8.04 (s, 1H), 7.93 (s, 1H), 7.53 (d, 1H), 4.00 (t, 2H), 3.24 (t, 2H), 2.42 (s, 3H).

MS (m/z): 381[MH]$^+$, 1Cl.

Intermediate 14

1,3-Dimethoxy-propan-2-ol

Metallic sodium (626 mg) was dissolved in anh. MeOH (7 mL), at 0° C., under $N_2$. When the solution was ready, 1,3-dichloro-propan-2-ol (1 mL) was added dropwise. NaCl precipitated immediately, and an additional portion of anh. MeOH (3 mL) was added and the reaction mixture was heated at reflux for 1.5 hr. It was then cooled down to r.t. and was diluted with $Et_2O$. The salts were filtered and the solvent was evaporated. The residue was distilled bulb to bulb to obtain the title compound as a clear oil (305 mg).

NMR ($^1$H,): δ 3.96 (m, 1H), 3.5-3.4 (m, 4H), 3.39 (s, 6H), 2.2 (bs, 1H).

Intermediate 15

1-Trityloxy-butan-2-ol

To a solution of 1,2-butandiol (2 g) in anh. pyridine (15 mL) was added triphenylmethyl chloride (8 g). The dark reaction mixture was heated at 100° C. for 8 hr and stirred at r.t. for 18 hr. The mixture was then poured in EtOAc/$H_2O$, the phases were separated and the organic layer was washed with sat. aq. NaCl and dried over $Na_2SO_4$. The solids were filtered and the solvent evaporated. The residual pyiridine was eliminated by filtration through a pad of silica gel (cHex/EtOAc 8/2). The solvent was evaporated and the residue was purified by flash chromatography (silica gel, cHex/EtOAc 95:5) to give the title compound (2.67 g)

NMR ($^1$H, $CDCl_3$): δ 7.42 (m, 6H),7.2 (m, 9H), 3.67 (q, 1H), 3.18 (q, 1H), 3 (q, 1H), 2.6 (d, 1H), 1.42 (q, 2H), 0.85 (t, 3H).

MS (m/z): [MH]$^+$.

Intermediate 16

7-(2,4-Dichloro-phenyl)-2-methyl-4-(1-trityloxymethyl-propoxy)-6,7dihydro-5H-pyrrolo[2,3-d]pyrimidine To a solution of intermediate 15 (180 mg) in anh. N-methyl pyrrolidone (1 mL), at r.t., under $N_2$, was added NaH 80%/oil (17 mg) and the reaction mixture was stirred at r.t. for 30 min. Intermediate 8 (85 mg) was then added and the reaction mixture was heated at 100° C. (screw cap vial) for 8 hr. It was then cooled down to r.t. and poured into $CH_2Cl_2$/$H_2O$. The phases were separated, the aqueous layer was extracted with $CH_2Cl_2$ (2×10 mL) and the combined organic extracts were dried over $Na_2SO_4$. The solids were filtered and the solvent evaporated to dryness in vacuo. The residue was purified by flash chromatography (silica gel cHex/EtOAc 9:1) to give the title compound as a clear oil (50 mg).

NMR ($^1$H): δ 7.7-7.2 (m, 18H), 5.5 (m, 1H), 3.96 (t, 2H), 3.3 (q, 1H), 3.15 (q, 1H), 3.05 (t, 2H), 2.4 (s, 3H), 1.65 (m, 2H), 0.8 (t, 3H).

MS (m/z): [MH]$^+$610.

Intermediate 17

1-Trityloxy-butan-2-ol

To a solution of 1,2-butandiol (2 g) in anh. pyridine (15 mL) was added triphenylmethyl chloride (8 g). The dark reaction mixture was heated at 100° C. for 8 hr and stirred at r.t. for 18 hr. The mixture was then poured in EtOAc/$H_2O$, the phases were separated and the organic layer was washed with sat. aq. NaCl and dried over $Na_2SO_4$. The solids were filtered and the solvent evaporated. The residual pyiridine was eliminated by filtration through a pad of silica gel (cHex/EtOAc 8:2). The solvent was evaporated and the residue was purified by flash chromatography (silica gel, cHex/EtOAc 95:5) to give the title compound as a yellow oil (2.67 g).

NMR ($^1$H, $CDCl_3$): δ 7.42 (m, 6H),7.2 (m, 9H), 3.67 (q, 1H), 3.18 (q, 1H), 3 (q, 1H), 2.6 (d, 1H), 1.42 (q, 2H), 0.85 (t, 3H).

MS (m/z): 332[MH]$^+$.

Intermediate 18

7-(2,4-Dichloro-phenyl)-2-methyl-4-(1-trityloxymethyl-propoxy)-6,7-dihydro-5H-pyrrolo[2,3-d]pyrimidine To a solution of intermediate 17 (180 mg) in anh. N-methyl pyrrolidone (1 ml), at r.t., under $N_2$, was added NaH 80%/oil (17 mg) and the reaction mixture was stirred at r.t. for 30 min. Intermediate 8 (85 mg) was then added and the reaction mixture was heated at 100° C. (screw cap vial) for 8 hr. It was then cooled down to r.t. and poured into $CH_2Cl_2$/$H_2O$. The phases were separated, the aqueous layer was extracted with $CH_2Cl_2$(2×10 mL) and the combined organic extracts were dried over $Na_2SO_4$. The solids were filtered and the solvent evaporated to dryness in vacuo. The residue was purified by flash chromatography (silica gel cHex/EtOAc 9:1) to give the title compound as a clear oil (50 mg).

NMR ($^1$H,$CDCl_3$): δ 7.7-7.2 (m, 18H), 5.5 (m, 1H), 3.96 (t, 2H), 3.3 (q, 1H), 3.15 (q, 1H), 3.05 (t, 2H), 2.4 (s, 3H), 1.65 (m, 2H), 0.8 (t, 3H)

MS (m/z): 610[MH]$^+$

Intermediate 19

2-[7-(2,4-Dichloro-phenyl)-2-methyl-6,7-dihydro-5H-pyrrolo[2,3-d]pyrimidin-4-yloxy]-butan-1-ol A solution of intermediate 18 (8 mg) in EtOH (1 mL) and TFA (0.5 mL) was stirred at r.t. for 48 hr. The solvents were then evaporated, the residue taken up in $CH_2Cl_2$ and washed with $H_2O$ (3×10 mL) to eliminate the residual acid. The organic layer was dried over $Na_2SO_4$, the solids were filtered and the solvent evaporated. The crude compound was purified by flash chromatography (silica gel cHex/EtOAc 9:1→8:2) to give the title compound (5 mg) as a clear oil.

MS (m/z): 368 [MH]$^+$.

NMR ($^1$H, DMSO-$d_6$): d 7.46 (d, 1H), 7.33 (d, 1H), 7.28 (dd, 1H), 4.87 (m, 1H), 3.99 (m, 2H), 3.85 (m, 2H), 3.09 (m, 2H), 2.38 (s, 3H), 1.69 (m, 2H), 1.03 (t, 3H).

Intermediate 20

(4.6-Dichloro-2-methyl-pyrimidin-5-yl)acetic acid methyl ester

Sodium (1.74 g, 3 eq) was added portionwise to anh. MeOH (60 mL), at 0° C., under $N_2$. After consumption of metallic sodium, acetamidine hydrochloride (7.06 g, 3 eq) was added. After 20 min. of stirring the precipitated NaCl was filtered off. A solution of 2-ethoxycarbonyl-succinic acid diethyl ester (6.04 g, 24.5 mmol) in anhydrous $CH_3OH$ (20 mL) was added to the solution of free acetamidine and the mixture was stirred at r.t. for 2 days. The reaction mixture was concentrated to dryness in vacuo and the yellow foam (8.69 g) obtained was then mixed with $POCl_3$ (6 eq) and $CH_3CN$ (10 Vol.) and heated at reflux for 18 hours. The resulting solution was cooled to r.t. and poured slowly into ice/water and conc. $NH_4OH$ with vigorous stirring. The product was extracted with EtOAc (3×). The combined organic extracts were washed with brine, dried over anh. $Na_2SO_4$, filtered and concentrated in vacuo. The crude oil was purified by flash chromatography (silica gel, cHex/EtOAc 8:2). The title compound was obtained as a yellow solid (98% in two steps)

NMR ($^1$H, $CDCl_3$): δ 5.85 (m, 1H), 5.15 (dq, 1H), 5.11 (dq, 1H), 3.61 (dt, 2H), 2.67 (s, 3H).

MS (m/z): 202 $[M]^+$ (2Cl).

Intermediate 21

2-(4,6-Dichloro-2-methyl-pyrimidin-5-yl)-ethanol

To a solution of intermediate 20 (4.0 g, 0.017 mol) in anh. THF (60 mL), at −78° C., under $N_2$, was added DIBA1-H 1M/THF (52.5 mL, 3 eq) dropwise. After the addition was complete, the reaction mixture was stirred at −30° C. for 3 hr. A Rochelle salt solution was then added at 0° C. and the phases were separated. The aqueous layer was extracted with EtOAc (2×50 mL) and the combined organic extracts were dried over anh. $Na_2SO_4$. The solids were filtered and the solvent evaporated. The title compound was obtained as a clear oil (3.1 gr, 89%) and was used in the next step without further purification.

NMR (1H, $CDCl_3$): δ 4.90 (t, 2H), 3.15 (t, 2H), 2.64 (s, 3H), 1.70 (bs, 1H).

MS (m/z): 207 $[MH]^+$

Intermediate 22

5-[2-tert-Butyl-dimethyl-silanoxy)-ethyl]-4,6-dichloro-2-methyl-pyrimidine

To a solution of intermediate 21 (3.1 g, 0.015 mol) in anh. DMF (100 mL), at 0° C., under $N_2$, were added imidazole (17 g, 17 eq), t-butyldimethylsilyl chloride (6.35 gr, 2.8 eq) and DMAP (catalytic amount). The solution was stirred at r.t. for 18 hr. EtOAc (100 mL) and sat.aq. $NH_4Cl$ (50 mL) were added and the phases were separated. The organic layer was washed with sat.aq. NaCl (2×100 mL) and dried over anh. $Na_2SO_4$. The solids were filtered and the solvent evaporated. The crude compound was purified by flash chromatography (silica gel, cHex/EtOAC 9:1) to give the title compound as a clear oil (4.6 g, 95%).

NMR ($^1$H, $CDCl_3$): δ 3.86 (t, 2H), 3.12 (t, 2H), 2.66 (s, 3H), 0.85 (s, 9H), 0.01 (s, 6H).

MS (m/z): 321 $[MH]^+$

Intermediate 23

(2,4-Bis-trifluoromethyl-phenyl)-{5-[2-(tert-butyl-dimethyl-silanoxy)-ethyl]-6-chloro-2-methyl-pyrimidin-4-yl}-amine To a solution of 2,4-bis-trifluoromethyl-aniline (984 µL, 1 eq) in anh. DMF (15 mL), at 0° C., under $N_2$, was added NaH 80%/oil (400 mg, 2.2 eq). The reaction mixture was stirred at 0° C. for 30 min and was then added to a solution of intermediate 22 (2 g, 6 mmol) in anh. DMF (15 mL) at r.t., under $N_2$. The reaction mixture was stirred at r.t. for 30 min. The excess NaH was carefully destroyed with sat.aq. NaCl and the reaction mixture was diluted with EtOAc. The phases were separated, the organic layer was washed with sat.aq. NaCl (2×30 mL) and dried over anh. $Na_2SO_4$. The solids were filtered and the solvent evaporated. The crude compound was purified by flash chromatography (silica gel, cHex/EtOAc 95:5→90:10).

The title compound was obtained as a clear oil (1.84 g, 56%).

NMR ($^1$H, $CDCl_3$): δ 8.61 (d, 1H), 8.04 (bs, 1H), 7.86 (s, 1H), 7.79 (d, 1H), 4.95 (t, 2H), 3.95 (t, 2H), 2.53 (s, 3H), 0.73 (s, 9H), −0.90 (s, 6H).

MS (m/z): 514 $[MH]^+$

Intermediate 24

2-[4-(2,4-Bis-trifluoromethyl-phenylamino)-6-chloro-2-methyl-pyrimidin-5-yl]-ethanol To a solution of intermediate 23 (1.84 g, 3.58 mmols) in anh. DMF (30 mL), at r.t., under $N_2$, was added $Et_3N.3HF$ (2.4 mL, 3 eq). The reaction mixture was stirred at r.t. for 18 hr. It was then diluted with cold sat.aq. NaCl (50 mL) and extracted with EtOAc (3×50 mL). The combined organic extracts were dried over anh. $Na_2SO_4$. The solids were filtered and the solvent evaporated. The title compound was obtained as a clear oil (1.4 gr, 98%) and was used in the next step without further purification.

NMR ($^1$H, $CDCl_3$): δ 8.59 (bs, 1H), 8.22 (d, 1H), 7.84 (s, 1H), 7.75 (d, 1H), 4.06 (t, 2H), 3.01 (t, 2H), 2.50 (s, 3H)

MS (m/z): 400 $[MH]^+$

Example 1

Synthesis of Representative Compounds of Structure (1a)

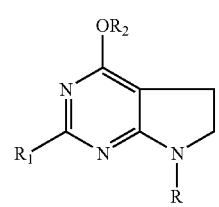

(1a)

7-(2,4-Dichlorophenyl)-4-(1-ethyl-propoxy)-2-methyl-6,7-dihydro-5H-pyrrolo[2,3-d]-pyrimidine (1-1)

To a suspension of NaH 80%/oil (4 mg) in anh. DMF (300 µL), at r.t., under $N_2$, was added 3-pentanol (15.5 µL) and the reaction mixture was heated at 50° C. for 15-20 min, or until a clear orange solution was obtained. Intermediate 8 (15 mg) was then added and the reaction mixture was heated at 100° C. (screw cap vial) for 60 min. It was then cooled down to r.t. and the solvent was evaporated. The residue was taken-up in $H_2O$ and the aqueous layer was extracted with $CH_2Cl_2$ (3×10 mL). The combined organic extracts were dried over $Na_2SO_4$, the solids were filtered and the solvent evaporated. The residue was purified by flash chromatography (silica gel, cHex/EtOAc 96:4) to obtain the title compound as a yellow oil (8 mg).

7-(2,4-Dichlorophenyl)-4-(1-isopropyl-2-methyl-propoxy)-2-methyl-6,7-dihydro-5H-pyrrolo-[2,3d] pyrimidine (1-2)

To a suspension of NaH 80%/oil (6 mg) in anh. DMF (0.5 mL), at r.t., under $N_2$, was added 2,4 dimethyl-3-pentanol (20 µL). The reaction mixture was heated at 50° C. for 15-20 min, or until a clear orange solution was obtained. Intermediate 8 (15 mg) was then added, and the reaction mixture was heated at 100° C. (screw cap vial) for 60 min. It was then cooled down to r.t. and poured in EtOAc/sat. aq. NaCl. The phases were separated and the organic layer was further washed with sat.aq. NaCl (2×10 mL) and dried over $Na_2SO_4$. The solids were filtered and the solvent was evaporated. The crude product was purified by flash chromatography (silica gel, cHex/EtOAc 95:5) to yield the title compound as a clear oil (9 mg)

7-(2,4-Dichlorophenyl)-4-isopropyl-3-methyl-butoxy)-2-methyl-6,7-dihydro-5H-pyrrolo-[2,3-d]pyrimidine (1-3)

To a suspension of NaH 80%/oil (4 mg) in anh. DMF (300 µL), at r.t., under $N_2$, was added 2,5-dimethyl-3-hexanol (18.6 mg) and the reaction mixture was heated at 50° C. for 15-20 min, or until a clear solution was obtained. Intermediate 8 (15 mg) was then added and the reaction mixture was heated at 100° C. (screw cap vial) for 60 min. It was then cooled down to r.t. and the solvent was evaporated. The residue was taken-up in $H_2O$ and the aqueous layer was extracted with $CH_2Cl_2$ (3×10 mL). The combined organic extracts were dried over $Na_2SO_4$, the solids were filtered and the solvent evaporated. The residue was purified by flash chromatography (silica gel, cHex/EtOAc 96:4) two times to obtain the title compound as a clear oil (2 mg).

7-(2,4-Dichlorophenyl)-4-(2-methoxy-1-methoxymethyl-ethoxy)-2-methyl-6,7-dihydro-5H-pyrrolo[2,3d]pyrimidine (1-4)

To a suspension of NaH 80%/oil (5.5 mg) in anh. DMF (300 µL), at r.t., under $N_2$, was added intermediate 14 (20 mg) and the reaction mixture was heated at 50° C. for 15-20 min, or until a clear solution was obtained. Intermediate 8 (20 mg) was then added and the reaction mixture was heated at 100° C. (screw cap vial) for 60 min. It was then cooled down to r.t. and the solvent was evaporated. The residue was taken-up in $H_2O$ and the aqueous layer was extracted with $CH_2Cl_2$ (3×10 mL). The combined organic extracts were dried over $Na_2SO_4$, the solids were filtered and the solvent evaporated. The residue was purified by flash chromatography (silica gel, cHex/EtOAc 96:4, then Tol/EtOAc 8:2) to obtain the title compound as a yellow oil (15.5 mg).

7-(2,4-Dichlorophenyl)-4-(2-ethyl-butoxy)-2methyl-6,7-dihydro-5H-pyrrolo[2,3-d]-pyrimidine (1-5)

To a solution of intermediate 8 (10 mg) in 2-ethyl-1-butanol (100 µL), at r.t., under $N_2$, was added NaH 80%/oil (10 mg). The reaction mixture was stirred at r.t. for 10 min, then heated at 60° C. for 15 hr. It was then cooled down to r.t. and poured in $CH_2Cl_2/H_2O$. The phases were separated and the organic layer was dried over $Na_2SO_4$. The solids were filtered and the solvent was evaporated to yield the title compound as a white foam (12 mg).

7-(2,4-Dichlorophenyl)-4-(2-ethoxy-1-ethoxymethyl-ethoxy)-2-methyl-6,7-dihydro-5H-pyrrolo[2,3d]pyrimidine (1-6)

To a suspension of NaH 80%/oil (4.0 mg) in anh. DMF (300 µl) at r.t., under $N_2$, was added 1,3-diethoxy-2-propanol (22.0 µl). The reaction mixture was stirred at 80° C. for 30 min. Intermediate 8 (15 mg) was then added and the reaction mixture was heated at 110° C. (screw cap vial) for 1 hr. It was then cooled down to r.t. and poured into EtOAc. The organic layer was washed with sat. aq. NaCl (3×10 mL) and dried over $Na_2SO_4$. The solids were filtered and the solvent evaporated. The crude product was purified by flash chromatography (silica gel, CHex/EtOAc 96:4) to give the title compound as a colourless oil (12.0 mg).

7-(2,4-Bis-trifluoromethyl-phenyl)4-(1-ethyl-propoxy)-2-methyl-6,7-dihydro-5H-pyrrolo[2,3-d]pyrimidine (1-7)

To a suspension of NaH 80%/oil (4.8 mg) in anh. DMF (300 µl), at r.t., under $N_2$, was added pentan-3-ol (17 µl). The reaction mixture was stirred at 80° C. for 15 min. Intermediate 13 (20 mg) was then added and the reaction mixture was heated at 110° C. (screw cap vial) for 1 h. It was then cooled down to r.t. and poured into EtOAc. The organic layer was washed with sat. aq. NaCl (3×10 mL) and dried over $Na_2SO_4$. The solids were filtered and the solvent evaporated. The crude product was purified by flash chromatography (silica gel, cHex/EtOAc 95:5) to give the title compound as a pale yellow solid (13.2 mg).

Example 1-1-13, 1-1-14 and 1-1-15 were prepared analogously, except that 2-trifluoromethyl-4-cyano-aniline, 2-chloro-3-amino-6-trifluoromethyl-pyridine and 2-cyano-4-trifluoromethyl-aniline were used respectively instead of 2,4-bis-trifluoromethyl-aniline in the production of intermediate 23

7-(2,4-Dichlorophenyl)-4-(1-ethyl-2-methyl-allyloxy)-2-methyl-6,7-dihydro-5H-pyrrolo[2,3 d]pyrimidine (1-8)

To a suspension of NaH 80%/oil (4.0 mg) in anh. DMF (300 µl) at r.t., under $N_2$, was added 2-methyl-1-penten-3-ol (15 mg). The reaction mixture was stirred at 80° C. for 30 min. Intermediate 8 (15 mg) was then added and the reaction mixture was heated at 110° C. (screw cap vial) for 1 hr. It was then cooled down to r.t. and poured into EtOAc. The organic layer was washed with sat. aq. NaCl (3×10 mL) and dried over $Na_2SO_4$. The solids were filtered and the solvent evaporated. The crude product was purified by flash chromatography (silica gel, cHex/EtOAc 96:4) to give the title compound as colourless oil (7 mg).

7(2,4-Dichlorophenyl)-4-(1-methoxymethyl-propoxy)-2-methyl-6,7-dihydro-5H-pyrrolo[2,3d]pyrimidine (1-9)

To a suspension of NaH 80%/oil (4.0 mg) in anh. DMF (300 µl) at r.t., under $N_2$, was added 1-methoxy-butan-2-ol (15 mg). The reaction mixture was stirred at 80° C. for 30 min. Intermediate 8 (15 mg) was then added and the reaction mixture was heated at 110° C. (screw cap vial) for 1 hr. It was then cooled down to r.t. and poured into EtOAc. The organic layer was washed with sat. aq. NaCl (3×10 mL) and dried over $Na_2SO_4$. The solids were filtered and the solvent evaporated.

The crude product was purified by flash chromatography (silica gel, cHex/EtOAc 9:1) to give the title compound as a colourless oil (11 mg).

2-[7-(2,4-Dichlorophenyl)-2-methyl-6,7-dihydro-5H-pyrrolo[2,3-d]pyrimidin-4-yloxy]butan-1-ol (1-10)

A solution of intermediate 16 (8 mg) in EtOH (1 mL) and TFA (0.5 mL) was stirred at r.t. for 48 hr. The solvents were then evaporated, the residue taken up in $CH_2Cl_2$ and washed with $H_2O$ (3×10 mL) to eliminate the residual acid. The organic layer was dried over $Na_2SO_4$, the solids were filtered and the solvent evaporated. The crude compound was purified by flash chromatography (silica gel cHex/EtOAc 9:1→8:2) to give the title compound (5 mg) as a clear oil.

2-[7-(2,4-Bis-trifluoromethyl-phenyl)-2-methyl-6,7-dihydro-5H-pyrrolo[2,3-d]pyrimidin-4-yloxy]-butan-1-ol (1-16) was prepared analogously, except that intermediate 13 was used instead of intermediate 8 in the preparation of intermediate 18.

7-(2.4-Dichlorophenyl)-2-methyl-4-(1-trifluoromethoxymethyl-propoxy)-6,7-dihydro-5H-pyrrolo[2,3 d]pyrimidine (1-11)

To a solution of intermediate 19 (6 mg) in anh. THF (1 mL), at r.t., under $N_2$, was added NaH 80%/oil (8 mg) and the reaction mixture was stirred at r.t. for 30 min, or until gas evolution ceased. A solution of trifluoromethyliodine 1.0M in THF (3 mL) was then added and the reaction mixture was stirred at r.t. (screw cap vial) for 24 hr. It was then poured into $CH_2Cl_2/NH_4Cl$ and the phases were separated. The aqueous layer was further extracted with $CH_2Cl_2$ (2×10 mL) and the combined organic extracts were dried over $Na_2SO_4$. The solids were filtered and the solvent evaporated to give the title compound still contaminated with the starting material.

Further representative compounds of this invention were prepared by the procedure set forth in the above examples.

All the analytical data are set forth in the following Table 1.

TABLE 1

| Cpd. N°. | R | $R_1$ | $R_2$- | Analytical Data |
|---|---|---|---|---|
| 1-1 | 2,4-dichlorophenyl | $CH_3$ | (sec-butyl ether group) | NMR ($^1$H, $CDCl_3$): δ 7.46 (d, 1H), 7.38, (d, 1H), 7.26 (dd, 1H), 5.18 (m, 1H), 3.96 (t, 2H), 3.04 (t, 2H), 2.39 (s, 3H), 1.69, (m, 4H), 0.94 (t, 6H). MS (m/z): 366 [MH]$^+$ 2 Cl. |
| 1-2 | 2,4-dichlorophenyl | $CH_3$ | (2,4-dimethylpent-3-yl ether) | NMR ($^1$H, $CDCl_3$): δ 7.46 (d, 1H), 7.40 (d, 1H), 7.27 (dd, 1H), 5.16 (t, 1H), 3.96 (t, 2H), 3.05 (t, 2H), 2.37 (s, 3H), 2.00 (m, 2H), 0.93 (d, 12H). MS (m/z): 394 [MH]$^+$ 2 Cl. |
| 1-3 | 2,4-dichlorophenyl | $CH_3$ | (branched alkyl ether) | NMR ($^1$H, $CDCl_3$): δ 7.51 (bs, 1H), 7.38 (d, 1H), 7.33 (bd, 1H), 5.39 (m, 1H), 4.03 (bt, 2H), 3.11 (t, 2H), 2.58 (bs, 3H), 1.95, m, 1H), 1.68-1.55 (m, 2H), 1.35 (m, 1H), 0.95 (m, 12H). MS (m/z): 408 [MH]$^+$ 2 Cl. |
| 1-4 | 2,4-dichlorophenyl | $CH_3$ | (1,3-dimethoxyprop-2-yl ether) | NMR ($^1$H,): δ 7.47 (d, 1H), 7.35 (d, 1H), 7.28 (dd, 1H), 5.64 (m, 1H), 3.97 (t, 2H), 3.68 (m, 4H), 3.41 (s, 3H), 3.40 (s, 3H), 3.10 (t, 2H), 2.43 (s, 3H). MS (m/z): 398 [MH]$^+$ 2 Cl. |
| 1-5 | 2,4-dichlorophenyl | $CH_3$ | (2-ethylbutyl ether) | NMR ($^1$H,): δ 7.46 (d, 1H), 7.37 (d, 1H), 7.27 (dd, 1H), 4.29 (d, 2H), 3.96 (t, 2H), 3.06 (t, 2H), 2.41 (s, 3H), 1.7-1.6 (m, 1H), 1.5-1.4 (m, 4H), 0.95 (t, 6H). MS (m/z): 380 [MH]$^+$ 2 Cl. |

TABLE 1-continued

| Cpd. N°. | R | R₁ | R₂- | Analytical Data |
|---|---|---|---|---|
| 1-6 | 2,4-dichlorophenyl | CH₃ | (1,3-diethoxyprop-2-yloxy) | NMR (¹H, CDCl₃): δ 7.42 (d, 1H), 7.31 (d, 1H), 7.23 (dd, 1H), 5.54 (m, 1H), 3.92 (t, 2H), 3.68 (d, 4H), 3.55 (m, 4H), 3.04 (t, 2H), 2.35 (s, 3H), 1.17 (t, 6H). MS (m/z): 426 [MH]⁺. |
| 1-7 | 2,4-bis-trifluoro-methyl-phenyl | CH₃ | (pentan-3-yloxy) | NMR (¹H, CDCl₃): δ 8.01 (s, 1H), 7.88 (d, 1H), 7.57 (d, 1H), 5.25 (bs, 1H), 3.97 (t, 2H), 3.10 (t, 2H), 2.46 (bs, 3H), 1.71 (m, 4H), 0.96 (t, 6H). MS (m/z): 434 [MH]⁺. |
| 1-8 | 2,4-dichlorophenyl | CH₃ | (2-methylenebut-3-yloxy) | NMR (¹H, CDCl₃): δ 7.46 (d, 1H), 7.36 (d, 1H), 7.28 (dd, 1H), 5.58 (bs, 1H), 5.02 (s, 1H), 4.91 (s, 1H), 3.98 (m, 2H), 3.08 (m, 2H), 2.41 (bs, 3H), 1.81 (m, 2H), 1.78 (s, 3H), 0.95 (t, 3H). MS (m/z): 378 [MH]⁺. |
| 1-9 | 2,4-dichlorophenyl | CH₃ | (1-methoxypentan-2-yloxy) | NMR (¹H, CDCl₃): δ 7.46 (d, 1H), 7.36 (d, 1H), 7.28 (dd, 1H), 5.43 (m, 1H), 3.98 (m, 2H), 3.62 (dd, 1H), 3.56 (dd, 1H), 3.41 (s, 3H), 3.08 (m, 2H), 2.42 (s, 3H), 1.75 (m, 2H), 0.98 (t, 3H). MS (m/z): 382 [MH]⁺. |
| 1-10 | 2,4-dichlorophenyl | CH₃ | (1-hydroxypentan-2-yloxy) | NMR (¹H, CDCl₃): δ 7.49 (t, 1H), 7.33 (t, 1H), 7.33 (s, 1H), 7.30 (d, 1H), 4.9 (m, 1H), 4.42 (m, 1H), 4.01 (t, 2H), 3.84 (m, 1H), 3.80 (m, 1H), 3.09 (t, 2H), 2.40 (s, 3H), 1.70 (m, 2H), 1.04 (t, 3H). MS (m/z): 368 [MH]⁺ 2 Cl. |
| 1-11 | 2,4-dichlorophenyl | CH₃ | (1-trifluoromethoxypentan-2-yloxy) | MS (m/z): 438 [MH]⁺. |
| 1-12 | 2,4-bistrifluoro-methylphenyl | CH₃ | (1-methoxypentan-2-yloxy) | NMR (¹H, CDCl₃): δ 7.99 (d, 1H), 7.86 (dd, 1H), 7.54 (d, 1H), 4.51 (dd, 1H), 4.37 (dd, 1H), 3.92 (t, 2H), 3.49 (s, 3H), 3.45 (m, 1H), 3.10 (t, 2H), 2.38 (s, 3H), 1.66 (m, 2H), 1.01 (t, 3H). MS (m/z): 450 [MH]⁺. |
| 1-13 | 2-trifluoromethyl-4-carboxyamino-phenyl | CH₃ | (pentan-3-yloxy) | NMR (¹H, CDCl₃): δ 8.19 (d, 1H), 8.00 (dd, 1H), 7.48 (d, 1H), 6.5-6.3 (bs, 1H), 5.7-5.5 (bs, 1H), 5.19 (m, 1H), 3.91 (t, 2H), 3.06 (t, 2H), 2.37 (s, 3H), 1.70 (m, 4H), 0.95 (t, 6H). |

TABLE 1-continued

| Cpd. N°. | R | $R_1$ | $R_2$- | Analytical Data |
|---|---|---|---|---|
| 1-14 | 3-(2-(1-ethyl-propoxy)-6-trifluoro-methyl)-pyridine | $CH_3$ | (structure) | NMR ($^1$H, CDCl$_3$): δ 8.20 (d, 1H), 7.41 (d, 1H), 5.93 (m, 2H), 4.20 (t, 2H), 3.05 (t, 2H), 2.32 (s, 3H), 1.80-1.65 (m, 8H), 0.96-0.90 (m, 12H). MS (m/z): 453 [MH]$^+$. |
| 1-15 | 2-cyano-4-trifluoro-methyl-phenyl | $CH_3$ | (structure) | NMR ($^1$H, CDCl$_3$): δ 7.92 (d, 1H), 7.88 (d, 1H), 7.75 (dd, 1H), 5.21 (m, 1H), 4.33 (t, 2H), 3.08 (t, 2H), 2.47 (s, 3H), 1.69 (m, 4H), 0.93 (t, 6H). IR (CDCl$_3$, cm$^{-1}$): 2228, 1590. |
| 1-16 | 2,4-bistrifluoro-methylphenyl | $CH_3$ | (structure with HO) | NMR ($^1$H, CDCl$_3$): δ 8.01 (bs, 1H), 7.88 (d, 1H), 7.32 (d, 1H), 4.48-4.38 (m, 2H), 3.95 (t, 2H), 3.84 (m, 1H), 3.12 (t, 2H), 2.35 (s, 3H), 1.60 (m, 2H), 1.04 (t, 3H) IR (nujol, cm$^{-1}$): 3393 MS (m/z): 436 [MH]$^+$. |

Example 2

CRF Binding Activity

CRF binding affinity has been determined in vitro by the compounds' ability to displace $^{125}$I-oCRF and $^{125}$I-Sauvagine for CRF1 and CRF2 SPA, respectively, from recombinant human CRF receptors expressed in Chinese Hamster Ovary (CHO) cell membranes. For membrane preparation, CHO cells from confluent T-flasks were collected in SPA buffer (HEPES/KOH 50 mM, EDTA 2 mM; MgCl$_2$ 10 mM, pH 7.4.) in 50 mL centrifuge tubes, homogenized with a Polytron and centrifuged (50,000 g for 5 min at 4° C.: Beckman centrifuge with JA20 rotor). The pellet was resuspended, homogenized and centrifuged as before.

The SPA experiment has been carried out in Optiplate by the addition of 100 μL the reagent mixture to 1 μL of compound dilution (100% DMSO solution) per well. The assay mixture was prepared by mixing SPA buffer, WGA SPA beads (2.5 mg/mL), BSA (1 mg/mL) and membranes (50 and 5 μg of protein/mL for CRF1 and CRF2 respectively) and 50 PM of radioligand.

The plate was incubated overnight (>18 hrs) at room temperature and read with the Packard Topcount with a WGA-SPA $^{125}$I counting protocol.

Example 3

CRF Functional Assay

Compounds of the invention were characterised in a functional assay for the determination of their inhibitory effect. Human CRF-CHO cells were stimulated with CRF and the receptor activation was evaluated by measuring the accumulation of cAMP.

CHO cells from a confluent T-flask were resuspended with culture medium without G418 and dispensed in a 96-well plate, 25,000 c/well, 100 μL/well and incubated overnight. After the incubation the medium was replaced with 100 μL of cAMP IBMX buffer warmed at 37° C. (5 mM KCl, 5 mM NaHCO$_3$, 154 mM NaCl, 5 mM HEPES, 2.3 mM CaCl$_2$, 1 mM MgCl$_2$; 1 g/L glucose, pH 7.4 additioned by 1 mg/mL BSA and 1 mM IBMX) and 1 μL of antagonist dilution in neat DMSO. After 10 additional minutes of incubation at 37° C. in a plate incubator without CO2, 1 μL of agonist dilution in neat DMSO was added. As before, the plate was incubated for 10 minutes and then cAMP cellular content was measured by using the Amersham RPA 538 kit.

Example 4

General Method for Radiolabelling the Compounds of Formula (I)

Materials and Methods

Unless otherwise stated reagents may be obtained in analytical grade from commercial sources (Aldrich, Fluka, BDH, Phoenix, etc.) and may be used without carrying further purification.

Quality control of [$^{11}$C]derivatives may be performed on a Gilson high performance liquid chromatography (HPLC) system (305-307 pumps, 118 UV-detector) connected with a Bioscan Flow-Count. Data analyses of the chromatograms were carried out with Laura 3 software (LabLogic Systems Limited).

Radiolabelling

Synthesis of [$^{11}$C]methyl iodide.

The production of [$^{11}$C]CO$_2$ via the $^{14}$N(p,α)$^{11}$C reaction may be carried out by irradiation of a nitrogen target (N$_2$, 99.99%) with 0.5% O$_2$ (99.99%) at a 17 MeV cyclotron (General Electric PET-trace). [$^{11}$C]CH$_3$I may be prepared by catalytic reduction (Ni) of [$^{11}$C]CO$_2$ to [$^{11}$C]CH$_4$ followed by gas phase iodination with I$_2$ using the PETtrace MeI Micro-Lab system(General Electric).

Example 5

Radiolabelling by [$^{11}$C]methylation of compounds (I)

[$^{11}$C]methyliodide may be passed through a reaction mixture containing the corresponding desmethyl precursor (0.7 mg) and an organic or inorganic base in dimethylformamide (100 μl) contained in a glass or a stainless steel container at room temperature for 2.5 min. After trapping, the reaction mixture may be heated at 85° C. for 10 min and injected onto a semi-preparative column for purification. Semi-preparative and analytical reverse phase HPLC columns were used for purification and quality control of the radioligand. The UV-detection wavelengths may be 254 nm for the semi-preparative HPLC and 254 nm for the analytical HPLC. [$^{11}$C](1-9) and [$^{11}$C](1-12) may be chromatographed on a Waters C18 Column (μ-Bondapak, 10μ, 300×7.8 mm).

Using 50% acetonitrile in 70 mM phosphate buffer as mobile phase at flow rate of 8 ml/min, [the final compounds may be eluted and fractionated.

The product fraction may be collected was evaporated to dryness, and reformulated in 0.9% NaCl. Sterile filtration of the product through a Millipore filter (Millex®-GS, 0.22 μm pore size) into a 11 ml evacuated sterile vial (Mallinckrodt) may provide a final product suitable for human use.

The radiochemical yields of the labeled compound varied between 40 and 50% corrected for decay with reference to iodomethane.

Quality controls may be performed on a Sphericlone column (ODS 250×4.6 mm). Using 50% Ethanol in 70 mM NaH$_2$PO$_4$ as mobile phase at flow rate of 1.5 ml/min, the final compounds may be eluted.

All publications, including but not limited to patents and patent applications, cited in this specification are herein incorporated by reference as if each individual publication were specifically and individually indicated to be incorporated by reference herein as though fully set forth.

It is to be understood that the present invention covers all combinations of particular and preferred groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

What is claimed is:

1. Compounds of formula (Ia) and stereoisomers and pharmaceutically acceptable salts thereof

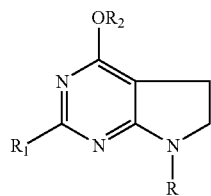

(Ia)

wherein

R is aryl or heteroaryl and R may be substituted by 1 to 4 groups selected from: halogen, C1-C6 alkyl, C1-C6 alkoxy, halo C1-C6 alkyl, C2-C6 alkenyl, C2-C6 alkynyl, halo C1-C6 alkoxy, —COR$_4$, nitro, —NR$_3$R$_4$, cyano and R$_5$;

R$_1$ is hydrogen, C1-C6 alkyl, C2-C6 alkenyl, C2-C6 alkynyl, halo C1-C6 alkyl, halo C1-C6 alkoxy, halogen, NR$_3$R$_4$ or cyano;

R$_2$ is CHR$_6$R$_7$;

R$_3$ is hydrogen or C1-C6 alkyl;

R$_4$ is hydrogen or C1-C6 alkyl;

R$_5$ is C3-C7 cycloalkyl, which may contain one or more double bonds, aryl or a 5-6 membered heterocycle;
wherein each R$_5$ may be substituted by one or more groups selected from: halogen, C1-C6 alkyl, C1-C6 alkoxy, halo C1-C6 alkyl, C2-C6 alkenyl, C2-C6 alkynyl, halo C1-C6 alkoxy, C1-C6 dialkylamino, nitro or cyano;

R$_6$ is hydrogen, C2-C6 alkenyl or C1-C6 alkyl, wherein R$_6$ may be substituted by one or more groups selected from: C1-C6 alkoxy and hydroxy; and R$_7$ is hydrogen, C2-C6 alkenyl or C1-C6 alkyl, wherein R$_7$ may be substituted by one or more groups selected from: C1-C6 alkoxy and hydroxyl.

2. Compounds, according to claim 1, wherein R$_1$ is C1-C3 alkyl or halo C1-C3 alkyl.

3. Compounds, according to claim 1, wherein R is selected from: 2,4-dichlorophenyl, 2-chloro-4-methylphenyl, 2-chloro-4-trifluoromethyl, 2-chloro-4-methoxyphenyl, 2,4-dimethylphenyl, 2-methyl-4-methoxyphenyl, 2-methyl-4-chlorophenyl, 2-methyl-4-trifluoromethyl, 2,4-dimethoxyphenyl, 2-methoxy-4-trifluoromethylphenyl, 2-methoxy-4-chlorophenyl, 3-methoxy-4-chlorophenyl, 2,5-dimethoxy-4-chlorophenyl, 2-methoxy-4-isopropylphenyl, 2-methoxy-4-trifluoromethylphenyl, 2-methoxy-4-isopropylphenyl, 2-methoxy-4-methylphenyl, 2-trifluoromethyl-4-chlorophenyl, 2,4-trifluoromethylphenyl, 2-trifluoromethyl-4-methylphenyl, 2-trifluoromethyl-4-methoxyphenyl, 2-bromo-4-isopropylphenyl, 4-methyl-6-dimethylaminopyridin-3-yl, 3,5-dichloro-pyridin-2-yl, 2,6-bismethoxy-pyridin-3-yl and 3-chloro-5-tricloromethyl-pyridin-2-yl.

4. A compound, according to claim 1, selected from the group consisting of:
7-(2,4-dichlorophenyl)-4-(1-ethyl-propoxy)-2-methyl-6,7-dihydro-5H-pyrrolo[2,3-d]-pyrimidine;
7-(2,4-dichlorophenyl)-4-(1-isopropyl-2-methyl-propoxy)-2-methyl-6,7-dihydro-5H-pyrrolo-[2,3-d]pyrimidine;
7-(2,4-dichlorophenyl)-4-(1-isopropyl-3-methyl-butoxy)-2-methyl-6,7-dihydro-5H-pyrrolo-[2,3-d]pyrimidine;
7-(2,4-dichlorophenyl)-4-(2-methoxy-1-methoxymethyl-ethoxy)-2-methyl-6,7-dihydro-5H-pyrrolo[2,3-d]pyrimidine;
7-(2,4-dichlorophenyl)-4-(2-ethyl-butoxy)-2-methyl-6,7-dihydro-5H-pyrrolo[2,3-d]-pyrimidine;
7-(2,4-dichlorophenyl)-4-(2-ethoxy-1-ethoxymethyl-ethoxy)-2-methyl-6,7-dihydro-5H-pyrrolo[2,3-d]pyrimidine;
7-(2,4-bis-trifluoromethyl-phenyl)-4-(1-ethyl-propoxy)-2-methyl-6,7-dihydro-5H-pyrrolo[2,3-d]pyrimidine;
7-(2,4-dichlorophenyl)-4-(1-ethyl-2-methyl-allyloxy)-2-methyl-6,7-dihydro-5H-pyrrolo[2,3-d]pyrimidine;
7-(2,4-dichlorophenyl)-4-(1-methoxymethyl-propoxy)-2-methyl-6,7-dihydro-5H-pyrrolo[2,3-d]pyrimidine;
2-[7-(2,4-dichlorophenyl)-2-methyl-6,7-dihydro-5H-pyrrolo[2,3-d]pyrimidin-4-yloxy]butan-1-ol;
7-(2,4-bis-trifluoromethyl-phenyl)-4-(1-methoxymethyl-propoxy)-2-methyl-6,7-dihydro-5H-pyrrolo[2,3-d]pyrimidine;

4-[4-(1-ethyl-propoxy)-2-methyl-5,6-dihydro-pyrrolo[2,3-d]pyrimidin-7-yl]-3-trifluoromethyl-benzamide;

4-(1-ethyl-propoxy)-7-[2-(1-ethyl-propoxy)-6-trifluoromethyl-pyridin-3-yl]-2-methyl-6,7-dihydro-5H-pyrrolo[2,3-d]pyrimidine; and 2-[4-(1-ethyl-propoxy)-2-methyl-5,6-dihydro-pyrrolo[2,3-d]pyrimidin-7-yl]-5-trifluoromethyl-benzonitrile.

5. A process for the preparation of a compound of formula (Ia) as claimed in claim 1, which comprises the reaction of a compound of formula (II), wherein L is a leaving group,

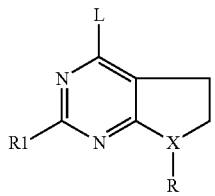

(II)

with the alcohol compound (III) HOCHR$_{2a}$R$_{3a}$ wherein X is nitrogen, R$_{2a}$ is a protected hydroxyl group or has the meaning defined in claim 1 for R$_2$ and R$_{3a}$ is a protected hydroxyl group or has the meaning defined in claim 1 for R$_3$.

6. A pharmaceutical composition comprising a compound according to claim 1, in admixture with one or more physiologically acceptable carriers or excipients.

7. A diagnostic formulation comprising a radiolabelled compound according to claim 1, in admixture with one or more physiologically acceptable carriers or excipients.

8. A method for the treatment of depression or anxiety, comprising administration of an effective amount of a compound according to claim 1 to a mammal in need of treatment thereof.

9. A method for the treatment of IBS (irritable bowel syndrome), comprising administration of an effective amount of a compound according to claim 1 to a mammal in need of treatment thereof.

* * * * *